(12) United States Patent
Grillini et al.

(10) Patent No.: US 11,966,511 B2
(45) Date of Patent: Apr. 23, 2024

(54) METHOD, SYSTEM AND COMPUTER PROGRAM PRODUCT FOR MAPPING A VISUAL FIELD

(71) Applicants: Rijksuniversiteit Groningen, Groningen (NL); Academisch Ziekenhuis Groningen, Groningen (NL)

(72) Inventors: Alessandro Grillini, Amersfoort (NL); Alejandro Hernández Garcia, Montreal (CA); Remco Jan Renken, Haren (NL)

(73) Assignees: Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 234 days.

(21) Appl. No.: 17/776,615

(22) PCT Filed: Nov. 13, 2020

(86) PCT No.: PCT/NL2020/050717
§ 371 (c)(1),
(2) Date: May 13, 2022

(87) PCT Pub. No.: WO2021/096361
PCT Pub. Date: May 20, 2021

(65) Prior Publication Data
US 2023/0022601 A1      Jan. 26, 2023

(30) Foreign Application Priority Data

Nov. 14, 2019 (EP) ...................... 19209204

(51) Int. Cl.
*G06F 3/01* (2006.01)
*G06V 40/18* (2022.01)

(52) U.S. Cl.
CPC ............ *G06F 3/015* (2013.01); *G06V 40/193* (2022.01)

(58) Field of Classification Search
CPC ........ G06F 3/015; G06V 40/193; A61B 3/024
(Continued)

(56) References Cited

U.S. PATENT DOCUMENTS 5,910,834 A * 6/1999 McClure ................. G06F 3/013
351/224
8,684,529 B2 * 4/2014 Johansson .............. A61B 3/024
351/224
(Continued)

OTHER PUBLICATIONS

Smith S M et al. "Threshold-free cluster enhancement: Addressing problems of smoothing, threshold dependence and localisation in cluster inference", Neuroimage, Elsevier, Amsterdam, NL, vol. 44, No. 1, Jan. 1, 2009 pp. 83-98.
(Continued)

*Primary Examiner* — Calvin C Ma
(74) *Attorney, Agent, or Firm* — Banner & Witcoff, Ltd.

(57) ABSTRACT

For measuring quality of view over a visual field of view of an eye, during a measuring period, deviations between gaze positions and associated stimulus positions where the stimulus to be followed was displayed when the gaze position was detected and magnitudes of the registered deviations arte determined. For each field portion of a map of a visual field of view, quality of view is determined in accordance with a quality of view estimates of associated ones of the registered deviations of which the associated stimulus positions are located relative to the gaze position so that the associated stimulus positions are in that field portion. For each of the associated ones of the registered deviations, the quality of view is estimated in accordance with the magnitude of that associated one of the registered deviations and with magni-
(Continued)

tudes of at least preceding or succeeding ones of the registered deviations.

18 Claims, 7 Drawing Sheets

(58) Field of Classification Search
USPC .......................................................... 345/156
See application file for complete search history.

(56) References Cited

U.S. PATENT DOCUMENTS

| | | |
|---|---|---|
| 2002/0047987 A1 | 4/2002 | Massengill et al. |
| 2002/0047991 A1* | 4/2002 | Jaggi ...................... A61B 3/024 |
| | | 351/209 |
| 2019/0110678 A1* | 4/2019 | Liu ........................ G16H 50/20 |

OTHER PUBLICATIONS

International Search Report and Written Opinion—PCT/NL2020/050717—mailing date Feb. 23, 2021.

* cited by examiner

No mask

TFCE, No mask

RNN, No mask

Scotoma mask 1

TFCE, Scotoma mask 1

RNN, Scotoma mask 1

Scotoma mask 2

TFCE, Scotoma mask 2

RNN, Scotoma mask 2

METHOD, SYSTEM AND COMPUTER PROGRAM PRODUCT FOR MAPPING A VISUAL FIELD

CROSS-REFERENCE TO RELATED APPLICATIONS

This application is a U.S. National Stage application under 35 U.S.C. § 371 of International Application PCT/NL2020/050717 (published as WO 2021/096361 A1), filed Nov. 13, 2020, which claims the benefit of priority to Application EP 19209204.7, filed Nov. 14, 2019. Benefit of the filing date of these prior applications is hereby claimed. Each of these prior applications is hereby incorporated by reference in its entirety.

FIELD AND BACKGROUND OF THE INVENTION

The invention relates to a method, a system and a computer program product for mapping a visual field of a person. Visual field mapping allows determining a map showing the quality of view over a visual field of a person around an optical axis of an eye or around optical axes of a pair of eyes. The obtained map of the quality of view over a field indicates the presence of visual field defects in portions of the visual field and, if any, the locations in the visual field of the portions of the visual field affected by visual field defects. Conventionally, visual field mapping involves the presentation of stimuli in several locations in the (potential) field of vision of an eye and registering whether the stimuli are seen or not. Locations where stimuli have not been seen reliably, obtain a low vision score in the visual field map.

A problem of conventional methods of visual field mapping is that these are either time consuming (Standard Automated Perimetry—SAP) or insensitive to minor defects (Frequency Doubling Technique—FDT) and cannot be carried out reliably on persons that are unable to concentrate, maintain a fixed gaze position during testing and follow instructions on how to respond to stimuli that have been seen.

U.S. patent application 2006/0114414 discloses measuring of a field of view of an eye by presenting stimuli in different positions relative to a current direction of view and measuring of the response time of a saccadic eye movement in response to a stimulus presented in a direction slightly off from a current direction of view and calculating the visual sensitivity in the direction where the stimulus has been presented as a function of the measured response time.

International patent application WO02012/141576 discloses determining visual field defects by presenting a sequence of visual stimuli in field of view of an eye, capturing movements of the eye in response to the stimuli and determining the saccadic reaction time to a new stimulus. If a shift in gaze corresponds to the location of a presented stimulus, the stimulus is registered as having been seen. By assessing the saccadic response time, accurate determination of visual defects is enabled.

U.S. patent application 2012/0022395 discloses analysis of oculomotor abnormalities of a human or animal subject by presenting stimuli, capturing eye movements in response to the stimuli, determining a value of at least one parameter of saccadic ocular movement and determining an abnormality on the basis of the determined value and a predetermined value of the parameter using an artificial intelligence module.

U.S. Pat. No. 9,730,582 discloses assessment of oculomotor response behavior and in particular assessment of degradation of visual processing under influence of diseases affecting visual sensitivity and resolution (such as retinal diseases and glaucoma), by measuring features of tracking behavior including pursuit initiation and precision and speed of pursuit and characteristics of a cloverleaf shape of anisotropy of directional gain of the pursuit response.

SUMMARY OF THE INVENTION

It is an object of the present invention to provide a solution that allows mapping the quality of view of an eye or eyes over a visual field, which is simple and accurate.

According to the invention, this object is achieved by providing a method according to claim 1. The invention can also be embodied in a system according to claim 14 and in a computer program product according to claim 15.

Because it suffices for the person of whom an eye is to be measured, to follow the stimulus to be followed as it moves and because, for each of the field portions, quality of view is determined in accordance with quality of view estimates of associated ones of the registered deviations of which the associated stimulus positions are located relative to the gaze position so that the associated stimulus positions are in that field portion, and, for each of the associated ones of the registered deviations, the quality of view is estimated in accordance with the magnitude of that associated one of the registered deviations and with magnitudes of at least preceding or succeeding ones of the registered deviations, the measurements can be carried out quickly and do not require accurate gazing to a stimulus prior to displaying of another stimulus in a position of the visual field of which vision is to be determined. In particular, the method is less sensitive to disturbances due to inaccurate gazing directions and levels of concentration and reaction time of a person whose eye is being measured.

The quality of view of a location in the visual field is determined in accordance with the magnitude of the deviation and preceding and/or succeeding deviations, when the stimulus is in that location of the visual field, because an eye is more strongly incited to shift the gaze position towards the stimulus, the further the stimulus position is away from the gaze position, so occurrence of a deviation of a large magnitude of a given duration is a stronger indication for a visual defect than occurrence of a deviation of a smaller magnitude of the same duration.

The quality of view of a location in the visual field is further determined in accordance with the duration of the sequence of deviations including that deviation and starting and ending with a deviation of a magnitude at or below a minimum threshold magnitude, because the duration of a cluster of deviations of which the deviation in a given location is a part is an indication of the sluggishness of centration of the gaze position towards the current position of the stimulus. Sluggishness of centration towards a given location is an indication for a visual defect in that location of the visual field.

For obtaining a variety of deviations and useful indications of types of visual dysfunctions, the stimulus to be followed is preferably moved with varying velocities. The velocity variations preferably include gradual increases and decreases of velocity (continuous curve of accelerations and decelerations) to incite an evenly distributed variety of magnitudes of deviation. The velocity variations may also include jumps in velocity to incite relatively large magnitudes of deviation. Furthermore, artefacts due to inaccurate stationary gazing to a stimulus to be followed are avoided particularly effectively if the stimulus position is moved continuously during the measurement period.

To avoid disturbances of the measurement results due to blinking or missing measurement values, gaze positions measured while the gaze position moves with a velocity over a threshold value (e.g. over 300 degrees/sec), stops and then moves again with a velocity over the threshold value, are replaced by interpolated gaze positions. For effectively removing such disturbances, positions in a predetermined range of time (e.g. 1/60-1/15 s) or sample number (e.g. 2-10 samples) prior to and after gaze positions measured while the gaze position moves with a velocity over the threshold value, stops and moves again with a velocity over the threshold value are replaced by interpolated gaze positions.

For the measurement according to the invention to be particularly accurate, it is preferred that only one moving stimulus to be followed and, more in particular, only one moving stimulus or only one stimulus at all is displayed.

According to a preferred embodiment, the method includes the use of a recursive neural network, for example a recursive neural network trained using gaze positions obtained by measurements of gaze positions of a healthy eye following a displayed stimulus to be followed.

According to an embodiment, indications for types of visual dysfunctions of the visual field as a whole can be determined from registered gaze positions and stimulus positions using the neural network. For example, visual view defects can be simulated by suppressing the displaying of the stimulus to be followed in predetermined field portions.

Indications for types of visual dysfunctions of the visual field as a whole, such as oculomotor delay, nystagmus, hypometric or hypermetric saccadic behavior, which provide pointers towards checks that could be useful for making a diagnosis, can be determined from registered gaze positions and stimulus positions in a particularly accurate manner using a recursive neural network trained using gaze positions obtained by measurements of gaze positions of a healthy eye following a displayed stimulus to be followed, visual view defects being simulated by suppressing the displaying of the stimulus to be followed in predetermined field portions.

In embodiments of the invention, indications for types of visual dysfunctions, which provide pointers towards checks that could be useful for making a diagnosis, can be determined particularly reliably if data inputted into the recursive neural network during training and during use of the trained recursive neural network include at least one of the following categories of data:

a maximum value of a correlation between gaze position velocity and stimulus position velocity;

temporal offset (lag) between gaze position and stimulus position;

temporal precision of gaze position relative to stimulus position;

variance explained by a Gaussian model fitted to a correlogram of gaze positions velocities and stimulus position velocities against time delay.

number of occurrences of a most likely deviation of the gaze position from the stimulus position;

average spatial offset (bias) between the gaze position and the stimulus position;

average deviation of the gaze position from the stimulus position; and variance of the deviation of the gaze position from the stimulus position explained by a Gaussian model fitted to a graph of occurrences of deviations in a plurality of ranges.

In a particularly accurate embodiment, the determination of the quality of view for each associated one of the registered deviations is carried out by integration over a series of the registered deviations, the series:

starting from a starting one of the series of the registered deviations having a magnitude at or below a minimum threshold magnitude $h_0$;

including a first succession of the registered deviations having magnitudes increasing up to a magnitude h of the associated one of the registered deviations;

including the associated one of the registered deviations; and including a second succession of the registered deviations having magnitudes decreasing from the magnitude h of the associated one of the registered deviations to a closing one of the series of the registered deviations, having a magnitude at or below the minimum threshold magnitude $h_0$; and forming an uninterrupted succession of the registered deviations of which, except for the starting one of the series of the registered deviations and the closing one of the series of the registered deviations, the magnitudes are larger than the minimum threshold magnitude $h_0$.

For appropriate weighting of the magnitudes of the series of deviations over which an integration is calculated, prior to the integration over the series of the registered deviations, the magnitudes of the series of the registered deviations that are larger than h are preferably reduced to a capping value in accordance with the magnitude h, the capping value preferably being equal to h.

The integration for each time point from the beginning of deviation from the threshold magnitude $h_0$ up to the magnitude h, until the deviation has returned to the threshold magnitude $h_0$ and capped at the magnitude h can for instance be carried out by cluster analysis such as calculation using a Threshold-Free Cluster Enhancement algorithm.

In an alternative embodiment, a particularly accurate determination of the quality of view for each field portion is carried out using a recursive neural network trained to obtain a recurrent neural model with:

training input including a series of training time points each including a stimulus position, being the position of the stimulus to be followed, and a gaze position of a healthy eye following the stimulus to be followed, and an indication for each training time point, whether the stimulus position relative to the gaze position is in a field portion where displaying of the stimulus to be followed was suppressed, and training output including a map of field portions where displaying of the stimulus to be followed was suppressed during a measurement session for obtaining the training input.

In operation, the method according to this embodiment preferably includes:

inputting a series of time points each including a stimulus position, being the position of the stimulus to be followed, and a gaze position of an eye to be examined following the stimulus to be followed;

the trained recursive neural network preferably classifying the visual qualities of the series of time points into scotoma time points at locations in the field of vision where vision is classified to be functional and non-scotoma time points at locations in the field of vision where vision is classified to be dysfunctional;

determining for each of the field portions which time points have a deviation such that the stimulus position relative to the gaze position is in that field portion; and generating a visual field map indicating, for each of the field portions, an aggregated vision quality value in accordance with the estimated visual qualities of the time points having a stimulus position determined to be in that field portion.

If the recursive neural network includes fully connected layers in which all output units are connected to all input units and vice versa and at least one gated recurrent unit that processes sequential information in a recurrent way with long short-term memory capabilities to capture time dependencies, the duration of respective deviations during which the registered stimulus positions and associated gaze positions have occurred are taken into account by the recursive neural network particularly effectively.

For a particularly accurate estimate of the visual field map, it is advantageous if the method furthermore includes:

capturing and inputting luminance of the stimulus and type of pursuit data during the measurement period;

at least two fully connected layers processing the luminance and pursuit data into categorical data into types of scotoma (e.g. Binasal hemianopsia, Bitemporal hemianopsia, Blind spot, Cortical spreading depression or Scintillating scotoma);

inputting a combination of the time points from the gated recurrent unit and the categorical data into a softmax classifier of the recurrent neural network; and the softmax classifier predicting for each time point whether, the stimulus position of that time point is in a location in the visual field, which is over a scotoma.

Further features, effects and details of the invention appear from the detailed description and the drawings.

DETAILED DESCRIPTION

The invention is further described with reference to examples of methods according to the invention and examples of tests for checking validity of the methods according to the invention.

For the methods according to the invention and the tests for checking validity of the methods according to the invention, the following hardware can be used:

a display screen 52 (see FIG. 2), for instance an LCD monitor; and a eye-tracker 53 for tracking gaze positions in a direction of view of an eye on the display, for instance a monitor-integrated eye-tracker: Eyelink 1000 (SR-Research, Ottawa, Canada); and a data processor system 54 connected to the display screen 52 for controlling the display screen 52 for displaying a visual stimulus 1 in a stimulus position (in this example the center of the stimulus blob) moving over the display screen 52 and connected to the eye tracker 53 for receiving data representing gaze positions from the eye tracker.

The data processor system 54 is programmed for carrying out a method according to the example described below. Data from the eye-tracker 53 are in this example acquired with a sampling rate of 1000 Hz and down sampled to temporally match the refresh rate of 240 Hz of the display screen 52.

Figure 2:
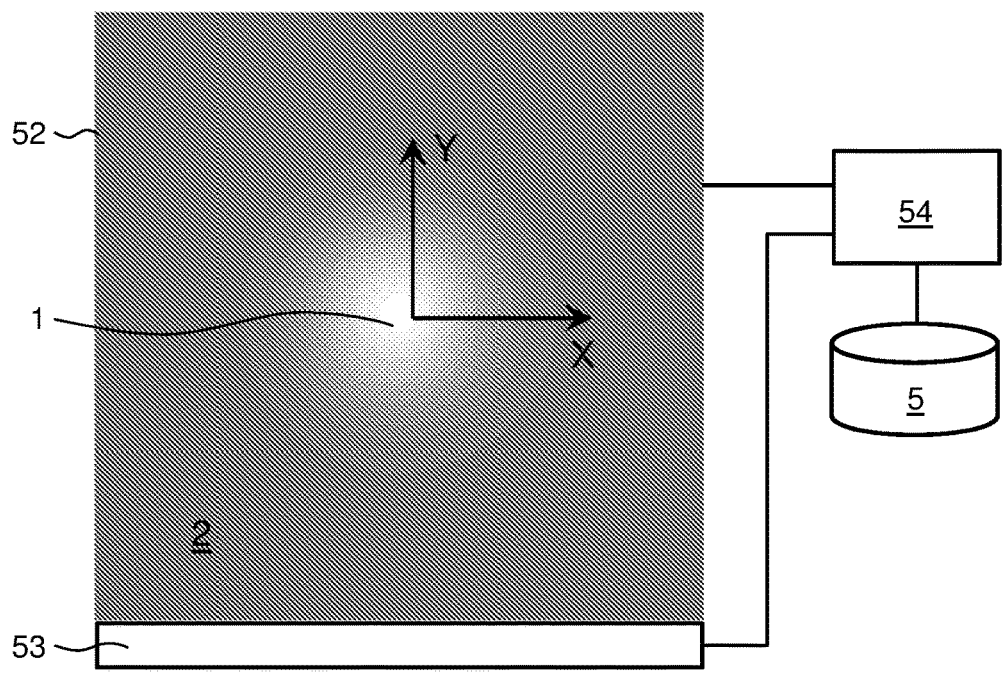
FIG. 2 is schematic representation of a system according to the invention with an example of a visual tracking stimulus being displayed.

In the present example, the visual stimulus to be followed is in the form of a Gaussian blob 1 of luminance moving on a uniform gray background 2 (~140 cd/m$^2$) (see FIG. 2). The movement has components in an up and down Y-direction and in a horizontal X-direction. The Gaussian blob 1 can be displayed within a range of contrast levels: at maximum contrast (50%) it has a peak luminance of ~385 cd/m$^2$, while when presented at minimum contrast (5%) it has a peak luminance of ~160 cd/m$^2$. The size of the Gaussian blob 1 (full width at half maximum) is 0.83 degrees of visual field, corresponding to size III of Goldman perimeter's stimulus, a commonly used perimetric device. Persons whose vision is tested are instructed to follow the stimulus 1 with their gaze of the eye being tested. In addition to the stimulus 1 to be followed, other visual stimuli can be displayed as well, which may be moving and/or stationary. In the present example, no other stimuli are displayed.

In step 3 (FIG. 1) a stimulus trajectory is created, which consists of a random path with the following constraints:

The stimulus trajectory 4 must be within the boundaries of the screen.

The stimulus trajectory cannot contain periodic autocorrelations. The stimulus trajectory 4 of this example is constructed by generating a velocity vector:

$$\vec{v}(t) = \begin{bmatrix} v_x \\ v_y \end{bmatrix}$$

where at each time point, velocity values for the horizontal ($v_x$) and vertical ($v_y$) components are drawn from a Gaussian distributions with a mean of 0 and separate standard deviations for horizontal ($\sigma_h$) and vertical ($\sigma_v$) directions. For example, for a standard screen resolution of 1920×1080 pixels the horizontal stand deviation can be $\sigma_h$=64.45 deg/s and the vertical stand deviation can be $\sigma_v$=32.33 deg/s. Preferably these $\sigma$ values may be adjusted based on screen dimension and/or specific application, e.g., obtaining a representation of a visual field map under specific conditions (e.g. taking measurements from a person with a known disease or known complaints).

The velocity vector can be low pass filtered by convolution with a Gaussian kernel such that a cutoff frequency is achieved, preferably around 10 Hz. Subsequently, via temporal integration, velocities are transformed to positions of the stimulus 1:

$$\vec{s}(t) = \begin{bmatrix} s_x \\ s_y \end{bmatrix}$$

Figure 1:
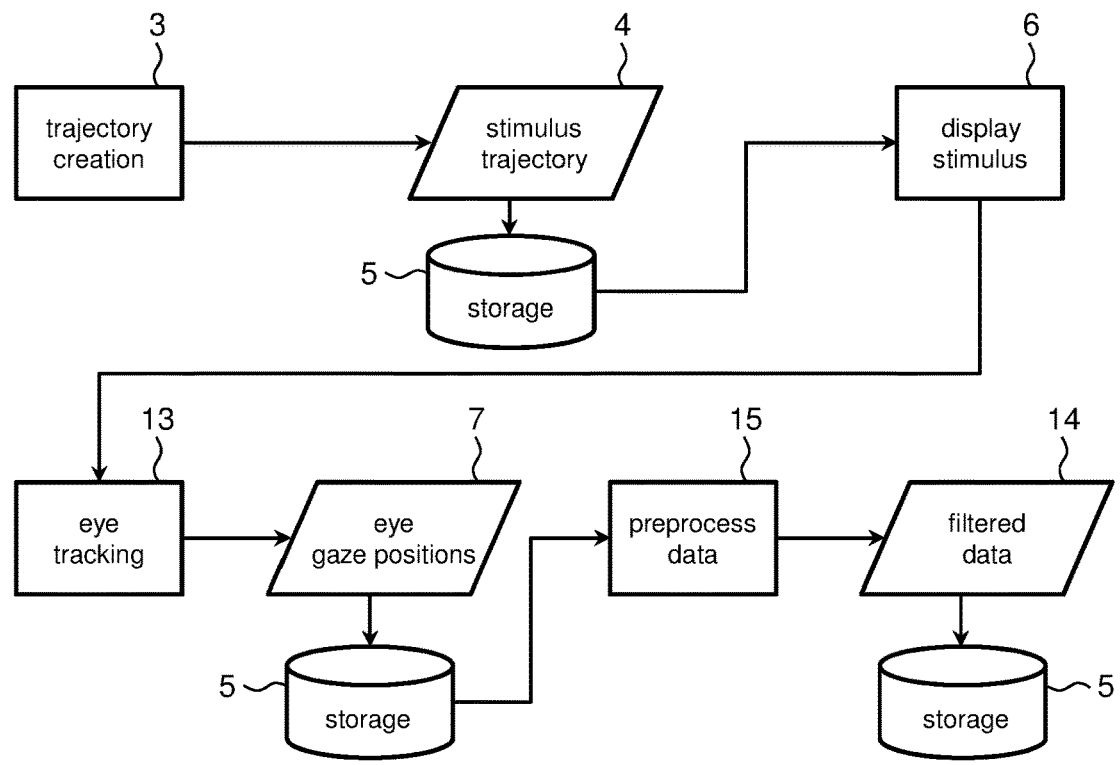
FIG. 1 is a flow chart of steps for acquisition of data regarding eye movements during a test.
Figure 3:
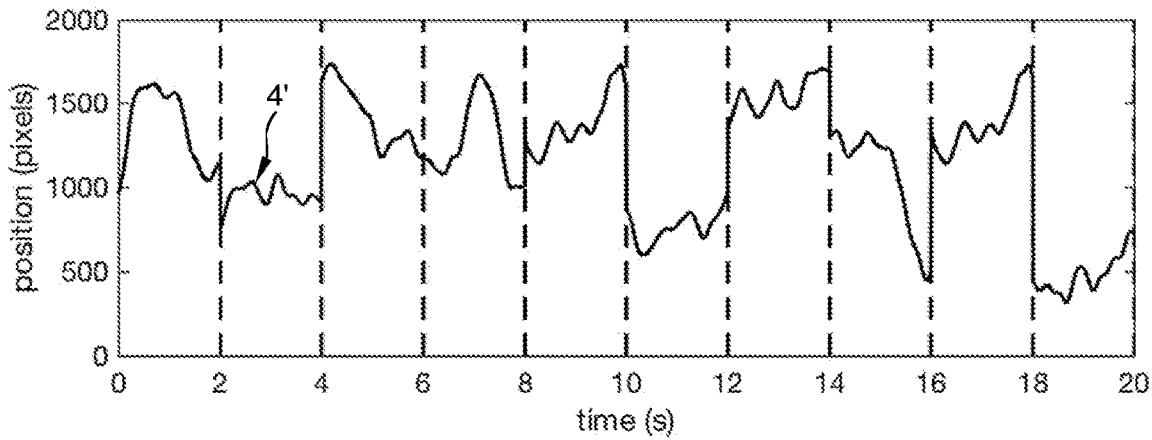
FIG. 3 is a graph showing of horizontal positions of the stimulus over time $_{Sh}(t)$.

To induce the person whose vision is tested to perform saccadic movements, quick displacements in random directions can be included in the trajectory of movement, as far as the displayed stimulus to be followed does not fall outside the boundary of the screen. This is achieved by adding such displacements, for instance each time after an interval of a fixed amount of seconds, preferably two, or after random time intervals. In FIG. 3 an example of a graph 4' of horizontal component $s_x$ of positions over time of a stimulus trajectory is shown. As is shown in FIG. 1, this created trajectory 4 is stored in a storage 5. In the present example all data are stored in the same storage 5, but sets of date may also be stored in several data storages.

Figure 5A:
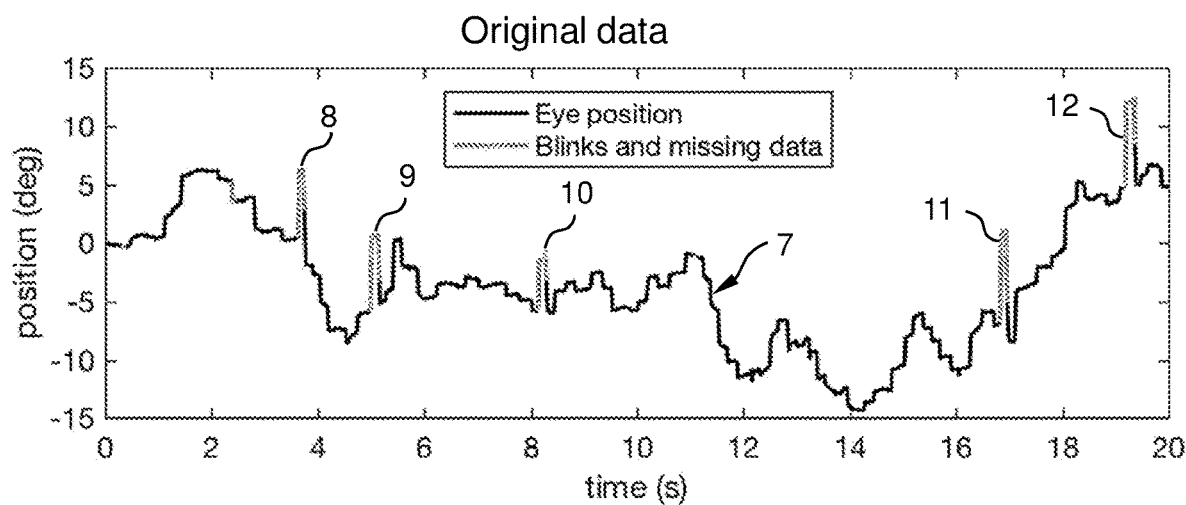
FIGS. 5A and 5B are graphs of observed viewing direction over time before and after filtering out of missing data and assumed displacements associated to blinks.

For the data acquisition the person whose vision is tested is positioned in front of the screen, for instance at a viewing distance of 60 cm. It is noted that instead of a screen other display techniques, such as holography, can be used as well. In step 6 (FIG. 1), the stimulus 1 is displayed on the screen 52 and moved, movement in x-direction being in accordance with the stimulus trajectory 4 which is read from the storage 5 and movement in y-direction being in accordance with another stimulus trajectory, preferably with the quick displacements in y-direction simultaneous with the quick displacements in x-direction. Head movement is preferably minimized, for instance by causing the head to rest on a head-chin-rest, or filtered out. Prior to each data acquisition session, the eye-tracker 53 is preferably calibrated using standard procedures, such as a nine point calibration. An eye tracking step 13 preferably includes a number of trials. In the present example, each trial lasts 20 seconds and is repeated six times. The acquisition results in horizontal and vertical gaze coordinates (expressed in pixels), for each time point. Pixel values are converted into degrees of visual angle so that a time-series of gaze positions $$\vec{p}(t) = \begin{bmatrix} p_x \\ p_y \end{bmatrix}$$

is obtained (see FIG. 5A). These data are also stored in the storage 5. In the present example, measurements are taken from one eye. However, measurements can also be taken simultaneously from two eyes, for instance if an indication of a visual aptitude to perform particular tasks is to be obtained.

For preprocessing, the time-series of gaze positions 7 is read from the storage 5. In the preprocessing step 15 of the present example, a first time period (e.g. the first 250 ms) of each time-series is discarded to avoid artefacts during settling in of the person whose vision is tested.

Other artefacts which are preferably avoided are artefacts due to blinking and missing data. Blink periods can for instance be identified by quick displacement back and forth forming spikes 8-12 in the graph 7 of gaze positions 7 (two short periods in which the absolute value of the first derivative of $\vec{p}(t)$ is above a predefined threshold and a short period in which it is 0). Time windows of each blink period found and a number of samples (e.g. five) on both sides of each blink period are preferably replaced by data determined using an autoregressive model using values of (e.g. ten) samples preceding and (e.g.) ten samples following the sample values to be replaced. Periods during which no data have been obtained can be expanded and replaced in the same manner as blink periods. If total data loss (due to blinks or otherwise) in a trial is very large (e.g. exceeds 25%), the entire trial is preferably removed from further analysis.

Figure 5B:
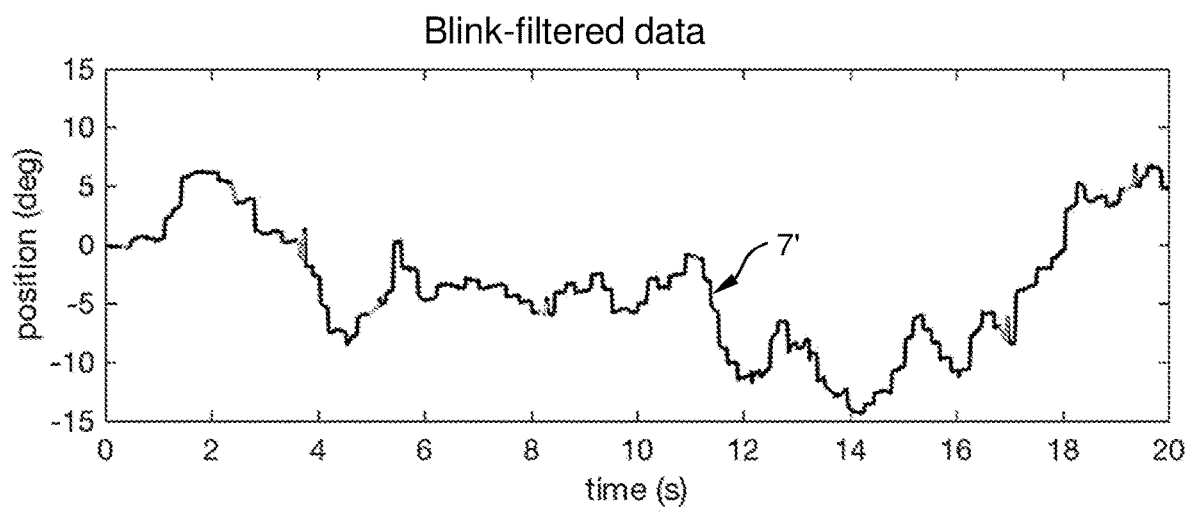

Thus in the present example a graph 7' (see FIG. 5B) of filtered data 14 (see FIG. 1) is obtained, which is stored in the storage 5 as well.

Figure 4:
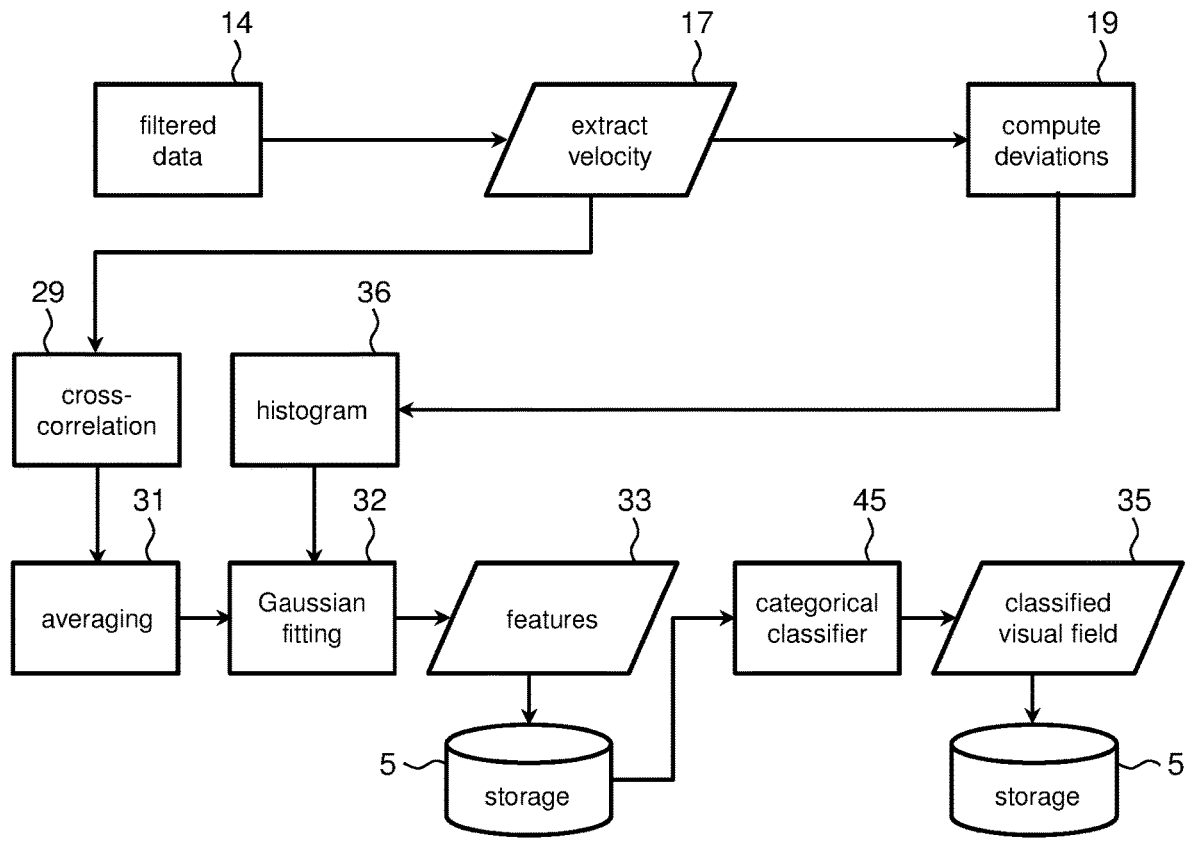
FIG. 4 is a flow chart of steps for extraction of spatiotemporal features and, based thereon, categorical classification of visual field defects.
Figure 7A:
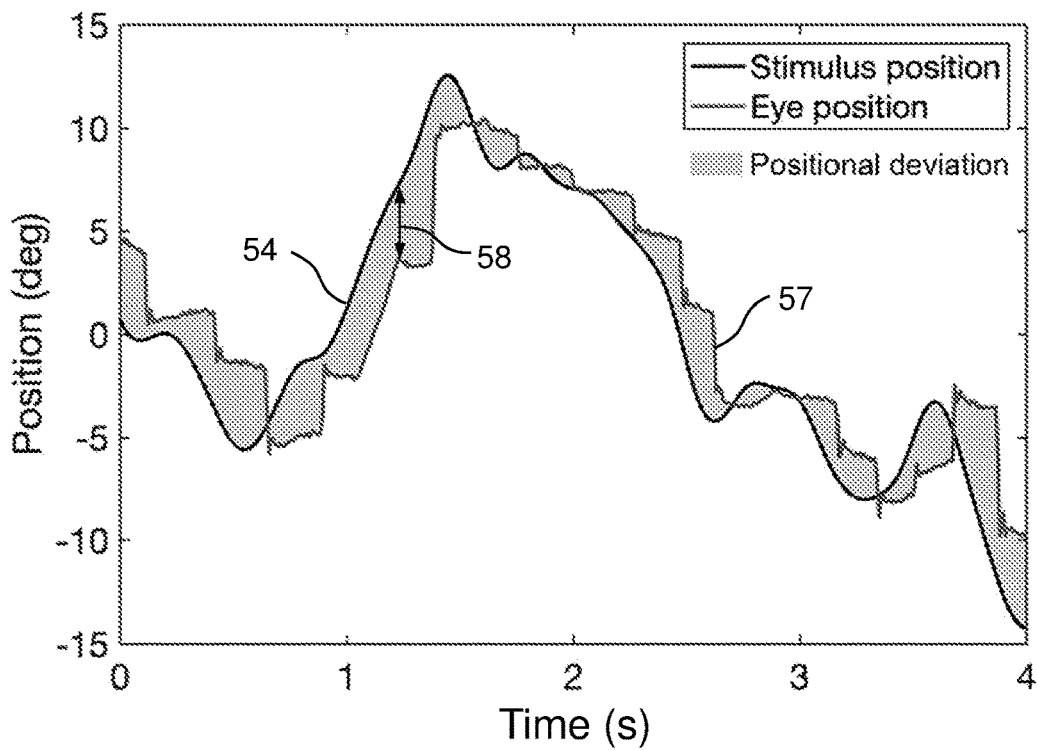
FIG. 7A is a graph of registered stimulus and gaze positions in an x-direction over time.

A positional error time-series is obtained by computing the distances, in this example the Euclidean distances, between $\vec{p}(t)$ and $\vec{s}(t)$, separately for horizontal and vertical components. FIG. 7A shows an example of a graph of horizontal positional deviations 58 of a blink filtered eye position graph 57 from a filtered stimulus position graph 54. Subsequently, a probability density distribution 36 (FIG. 4, stage 36 and FIG. 7B) is computed for the overall positional error time-series, for instance by computing a histogram using bins of 1 degree of visual field, spanning from −20 to +20 degrees.

Figure 6A:
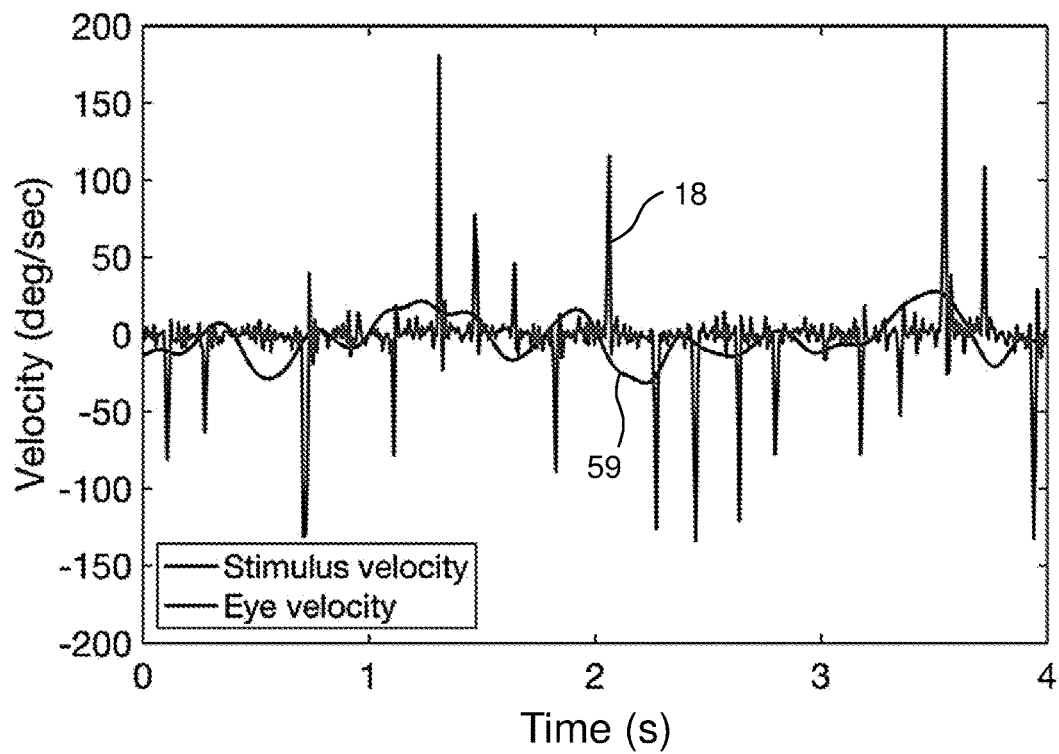
FIG. 6A is a graph of registered velocity of changes of viewing direction over time.

In step 17, time-series of gaze positions 7' $\vec{p}(t)$ and stimulus positions $\vec{s}(t)$ of the filtered data 14 are transformed into respective velocities $\vec{v}_p(t)$ and $\vec{v}_s(t)$ by taking the first order temporal derivative. This results in a time series of velocities. An example of a graph 18 of a time series of such velocities of the gaze position of the eye $\vec{v}_p(t)$ in x-direction is shown in FIG. 6A. An associated time series of such velocities of the stimulus position $\vec{v}_s(t)$ in x-direction is shown as graph 59.

Figure 6B:
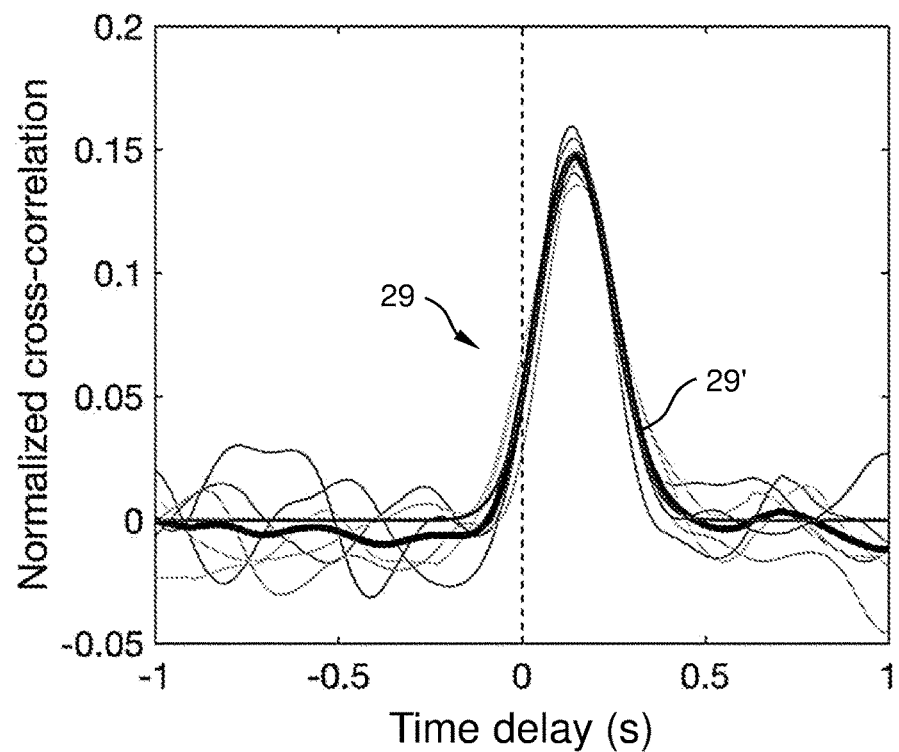
FIG. 6B is a graph (cross-correlogram) of time delay against cross-correlations between stimulus velocity and ocular velocity after the time delay.
Figure 7B:
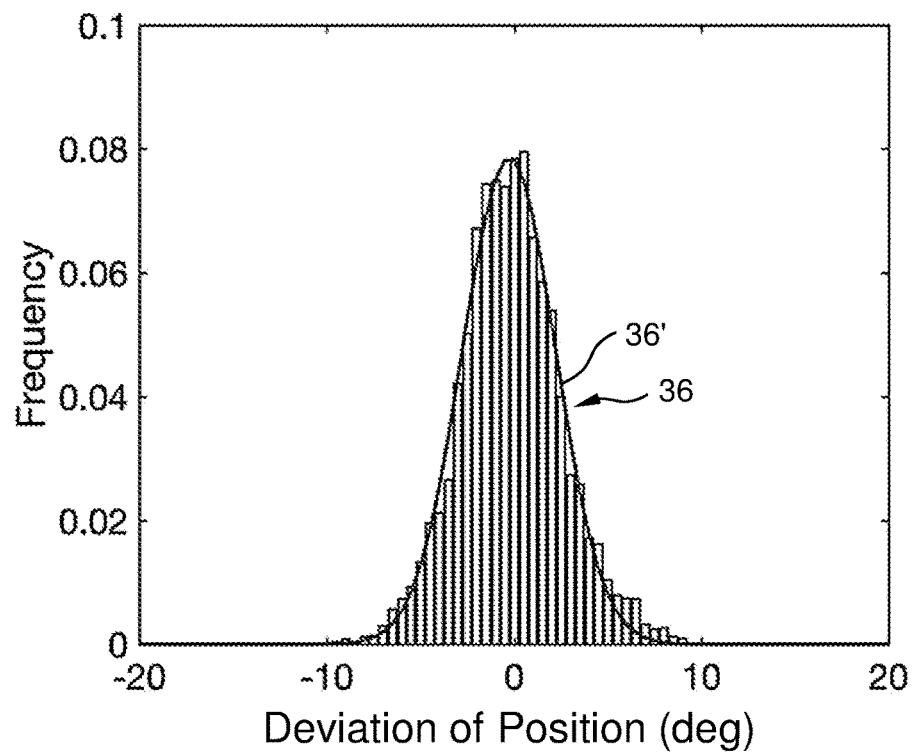
FIG. 7B is a graph of the probability density distribution of positional deviations between gaze position and stimulus position.

Normalized time-shifted cross-correlations 29 (FIG. 4, stage 29 and FIG. 6B) between filtered time-series of velocities of the stimulus position $\vec{v}_s$ and velocities of the gaze position $\vec{v}_p$ are determined for horizontal and for vertical components separately. The time-shift may for instance range from −1 s to +1 s with step-size of 1 IFI (inter-frame interval). In this example, each data-acquisition of 20 seconds leads to a set of cross-correlations. In this example, the six sets of cross-correlations are averaged in step 31. An example of achieved cross-correlograms of velocities (CCG) 29 is shown in FIG. 6B. A density distribution of positional deviations (PDD) as the histogram 36 (FIGS. 4 and 7B), of which an example is shown in FIG. 7B, is determined from the filtered time-series of the velocities of the stimulus position $\vec{v}_s$ and the gaze position $\vec{v}_p$ for horizontal and for vertical components separately. In step 32, both the correlogram 29 and the histogram 36 are fitted with a Gaussian model, for their respective horizontal and vertical components separately, to obtain Gaussian fits 29', 36'. In step 33 the following parameters are extracted from each Gaussian fit 29', 36',: amplitude, $\mu$, $\sigma$, and $R^2$:
CCG

- amplitude: maximum value of the correlation between $\vec{v}_p$ and $\vec{v}_s$;
- $\mu$: temporal offset (lag) between eye and stimulus;
- $\sigma$: temporal precision of tracking performance (i.e. how much time is needed to the observer to estimate target's position);
- $R^2$: variance explained of the temporal Gaussian model.

PDD

- amplitude: occurrences of the most likely positional deviation;
- $\mu$: spatial offset (bias) between eye and stimulus;
- $\sigma$: spatial precision of tracking performance;
- $R^2$: variance explained of the spatial Gaussian model.

The eight listed spatio-temporal features of the relationship between the stimulus positions and the associated gaze positions over a measurement session are obtained in horizontal direction and in vertical direction, so a total of 16 spatio-temporal features is obtained and stored in the storage 5. In step 45 (FIG. 4), these spatio-temporal features are inputted into a categorical classifier 45 and processed thereby to determine an estimate of the classification 35 of the visual field as a whole.

Figure 9:
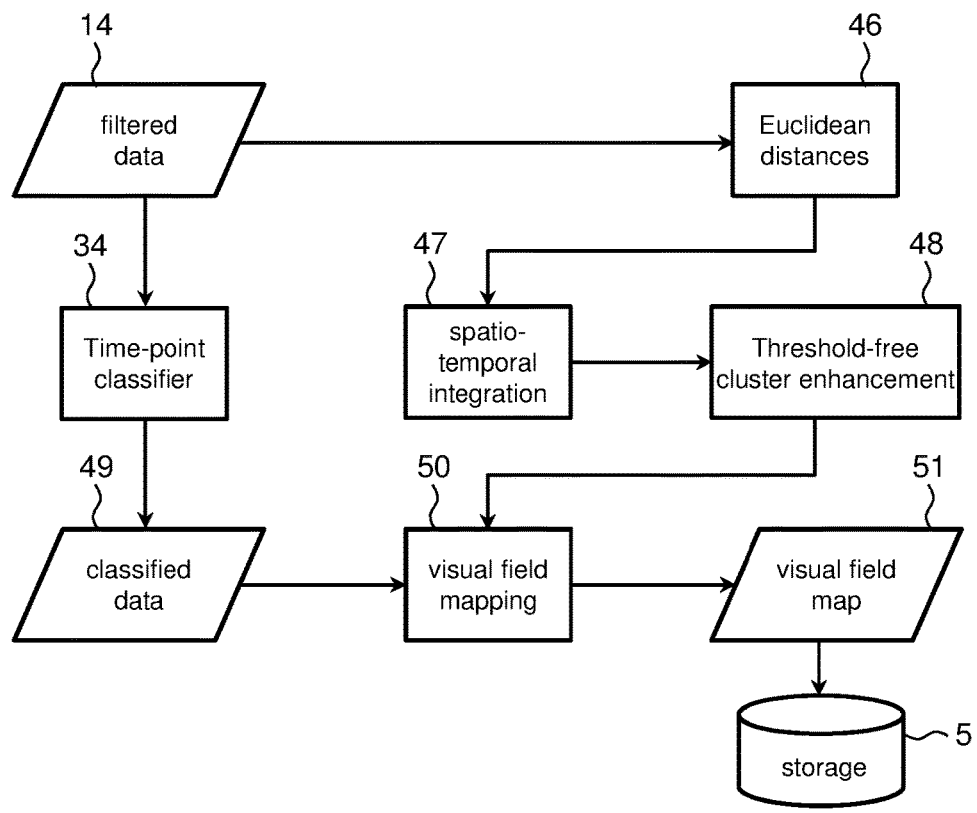
FIG. 9 is a flow chart of steps for determining a visual field map of an eye from the data regarding eye movements during the test.

For determining a quality map of the visual field of an eye of which ocular movement has been measured a spatio-temporal integration of positional deviations between the stimulus location and the gaze location can be used. The gaze position of an eye of a person with reduced oculomotor functionality, e.g. reduced vision in portions of the visual field of an eye, will deviate more, and for longer periods of time, from the position of the target stimulus to be followed than the gaze position of a person with a healthy oculomotor functionality will deviate from the position of the target stimulus to be followed. The magnitude h(t) of the positional deviation 46 (FIG. 9) as a function of time can be defined as:

$$h(t) = \sqrt{(p_x(t)-s_x(t))^2 + (p_y(t)-s_y(t))^2}$$

A spatio-temporal integration 47 is performed using a Threshold-Free Cluster Enhancement algorithm (TFCE). Such an algorithm is described in Threshold-free cluster enhancement: addressing problems of smoothing, threshold dependence and localisation in cluster inference; Smith, S. M. & Nichols, T. E.; Neuroimage 44, 83-98 (2009). In the present implementation of this algorithm, for each registered combination of a stimulus position and a gaze position, the TFCE score is given by the sum of the magnitudes of all "supporting sections" of a cluster formed by a deviation curve underneath it; starting as the magnitude h is incrementally raised from $h_0$ up to the magnitude $h_t$ of a given time point t, the time course is thresholded at h, and the single contiguous cluster containing t ends as the magnitude returns to $h_0$. The surface area under the deviation curve defines the spatio temporal integration score for that magnitude h. This score is the magnitude h (raised to some power H) multiplied by the cluster extent in time e (raised to some power E), using the following formula:

$$D_{STI} \int_{h=h_0}^{h_p} e(h)^E h^H dh$$

This integral is implemented as a discrete sum using a finite step-size, dh (for example, dh=1/2500 of the maximum of h); $h_0$ is typically the minimum of h, and E and H can be set a priori (optimized using simulated visual field effects). The result is a time-series of positional deviations 48, each weighted for their spatio-temporal integrated characteristics: $D_{STI}$. Thus, for each positional deviation, the value $D_{STI}$ depends on the magnitude of the deviation and the time it takes until the deviation curve of which it is a part has returned to a magnitude $h^0$. The value $D_{STI}$ assigned to a positional deviation 48 can also be defined as forming an integral for each time point from a beginning of deviation up to the magnitude h, until the deviation has returned to the magnitude $h_0$ and capped at the magnitude h.

For determining a quality of view field map 51 of the eye from which measurements have been made, each occurrence of the input time-series $D_{STI}$ is associated with its horizontal and vertical components, respectively $D'_x = p_x(t) - s_x(t)$ and $D'_y = p_y(t) - s_y(t)$, which form the x- and y- components of the position of the stimulus relative to the center of the visual field, which include for each time point an estimate of the quality of view at that position relative to the center of the visual field.

In step 50, these components are mapped onto a Cartesian plane of which the origin represents the center of gaze of the eye. In this way, the Cartesian plane forms a representation of the visual field and its center represents the fovea.

In step 50, spatial binning may be applied (e.g. with a bin size equal to one degree of visual field). The value at each bin is then the average of the $D_{STI}$ values within that bin.

Finally, the calculated map 51 can be stored in the storage 5 and displayed, for instance in a 50×40 grid, covering ±25 degrees of visual field. In this map the severity of visual field loss is indicated (for instance color-coded or in gray scale) and the map can readily be interpreted by ophthalmologists.

Figure 10A:
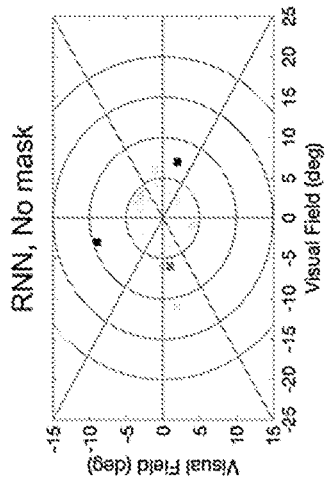
FIG. 10A is an example of a map of a visual field with no visual field defects.
Figure 10B:
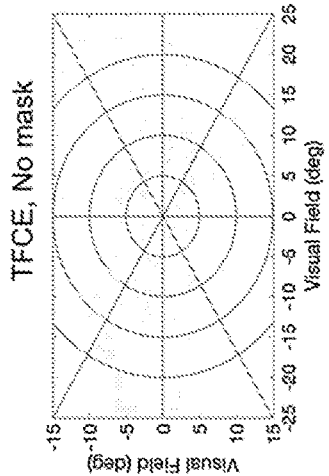
FIG. 10B is a map of a visual field obtained from measurement data acquired from a test of a healthy eye (i.e. to which the map shown in FIG. 10A applies) without suppression of stimulus display in predetermined positions, by threshold-free cluster enhancement (TFCE) processing.
Figure 10C:
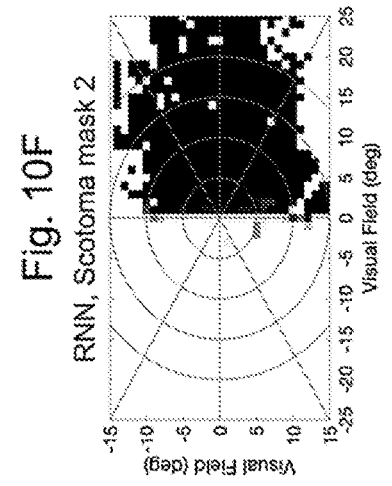
FIG. 10C is map of visual defects obtained from measurement data acquired from a test of performance of a healthy eye (i.e. to which the map shown in FIG. 10A applies) without suppression of stimulus display in predetermined positions, by recursive neural network (RNN) processing.
Figure 10D:
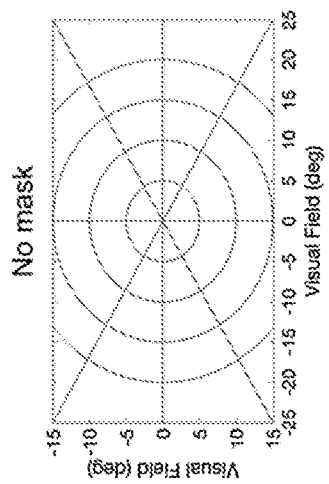
FIG. 10D is a map of simulated scotoma locations (of a peripheral loss visual defect pattern type) formed by locations where display of the stimulus was suppressed when testing performance of the healthy eye.
Figure 10E:
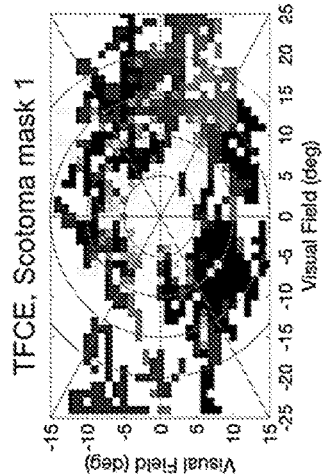
FIG. 10E is a map of visual field obtained from measurement data acquired from a test of performance of the healthy eye with suppression of stimulus display in predetermined positions as shown in FIG. 10D, by TCFE processing.
Figure 10F:
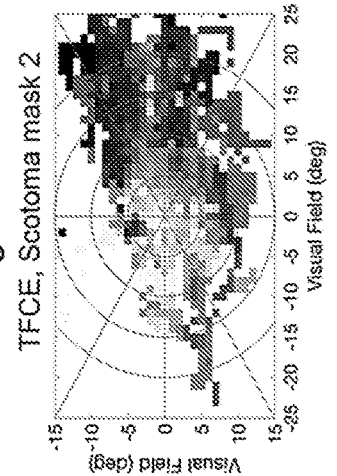
FIG. 10F is map of visual defects obtained from measurement data acquired from a test of performance of the healthy eye with suppression of stimulus display in predetermined positions as shown in FIG. 10D, by RNN processing.
Figure 10G:
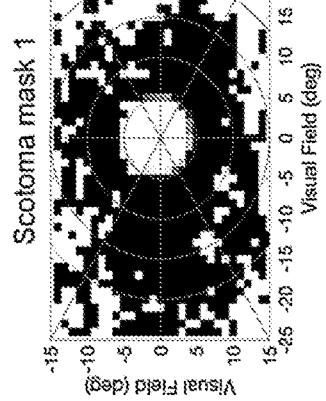
FIG. 10G is a map of simulated scotoma locations (of a hemifield loss visual defect pattern type) formed by the locations where display of the stimulus was suppressed when testing performance of the healthy eye.
Figure 10H:
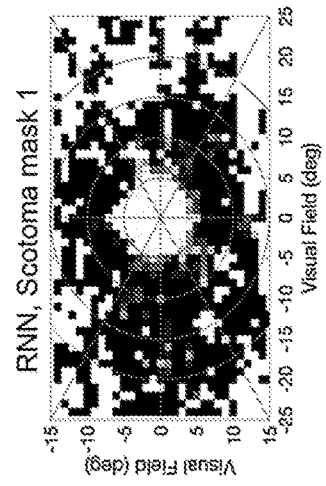
FIG. 10H is a map of visual field obtained from measurement data acquired from a test of performance of the healthy eye with suppression of stimulus display in predetermined positions as shown in FIG. 10G, by TFCE processing.

Examples of such visual field maps, resulting from experimental implementation of the described spatio-temporal integration using TFCE method, are shown in FIGS. 10B, 10E, and 10H.

Figure 8:
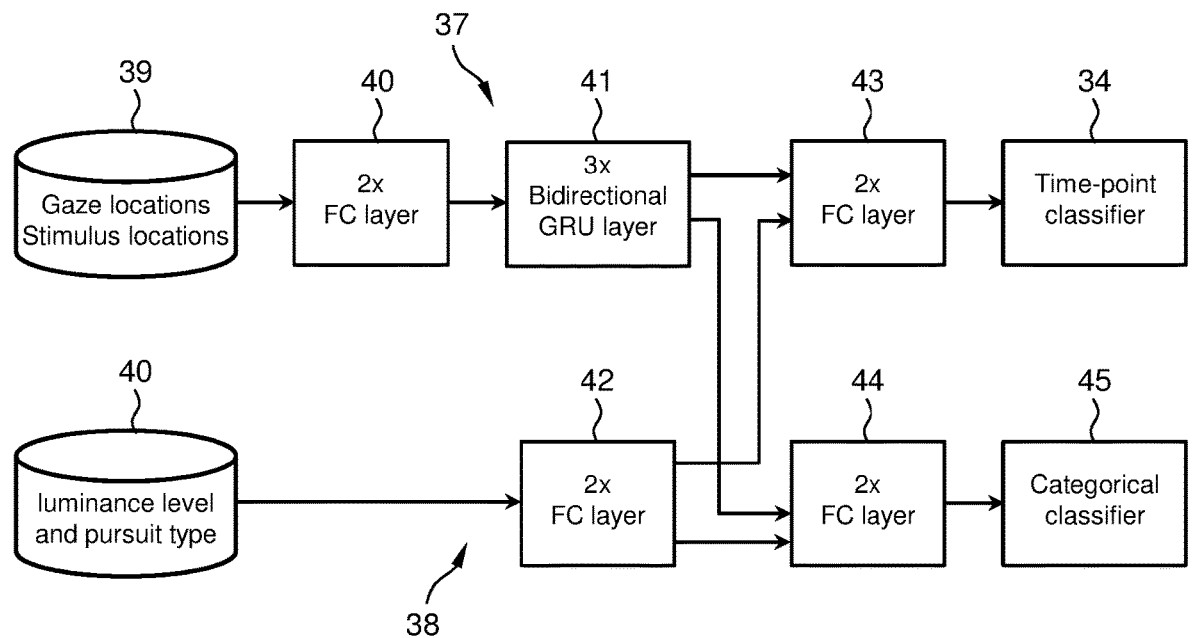
FIG. 8 is a flow chart of stadia of the architecture of a deep recursive neural network for determining categorical (visual defect type) classifiers and time point classifiers.

As an alternative to the spatio-temporal integration method, a map of quality of view of a visual field of an eye can be estimated from the measurement results using a trained recursive neural network. The recursive neural network can be trained to obtain artificial intelligence classifiers 34 and 45 (FIG. 8). As training input x, a time series of gaze positions $\vec{p}(t)$ and stimulus positions $\vec{s}(t)$, as well as the luminance and type of pursuit of the stimulus is used. As training output y, a known map of visual field defects as simulated during the acquisition of the test data is used and, for each time point, it is determined whether the stimulus lies in a location in which a scotoma was simulated. The locations of simulated scotoma are predetermined surface portions of the visual field and the scotoma are simulated by suppressing display of the stimulus to be followed in these predetermined surface portions of the visual field. The pattern of surface portions of the visual field where display of the stimulus to be followed is suppressed form a virtual mask, which masks the surface portions of the visual field where scotoma are to be simulated by suppressing displaying the visual stimulus 1 to be followed when it is in a position in these surface portions. This virtual mask moves relative to the display area along with movements of the gaze position.

The deep recursive neural network consists of two streams 37, 38 (see FIG. 8) that initially process a series of time points 39 each including x-coordinates and y-coordinates of a gaze position $\vec{p}(t)$ and of a stimulus position $\vec{s}(t)$ 39 and the luminance of the stimulus and pursuit type 40 separately. In particular, the time point classifying stream 37 that processes the time series data consists of two fully connected (FC) layers 40, that is, layers in which all the output units are connected to all input units and vice versa, with 16 nodes each. After the FC layers 40, the sequential stream is followed by three gated recurrent units (GRU) 41, that is, layers that process sequential information in a recurrent way with long short-term memory capabilities to capture time dependencies, formed by 32, 64 and 64 nodes each. The categorical classifying stream 38 consists of two fully connected layers 42 with two and four units each, which process the luminance and pursuit information. The outputs of the two layers 41 and 42 are concatenated conveniently and are both processed by two separate FC layers 43, 44.

All the time points from the sequential data (from GRU layers 41) are merged with the categorical data (obtained with luminance level and pursuit type information from FC layers 42) and processed by two FC layers 43 with 32 and two nodes, respectively. The output of these FC layers 43 is the input of a softmax classifier 34 that predicts whether, for each time point, the stimulus position is in a location in the visual field, i.e. relative to the gaze position, which is over a scotoma.

The other stream also merges the last time points from the sequential data (from GRU layers 41) with the categorical data (from FC layers 42) and processes these data by two FC layers 44 with 32 and four nodes, respectively. The output of these FC layers 44 is the input of another softmax classifier 45 that predicts the visual field condition (categorical classifier, 45).

Cross-entropy loss is used to define the cost function of the model:

$$J(\theta) = -\alpha \sum_{c=1}^{M_s} y_{s,c} \log(p_{s,c}) - \beta \sum_{c=1}^{M_d} y_{d,c} \log(p_{d,c})$$

where M is the number of classes, y is the ground truth label (obtained from the simulated visual field map) and p is the predicted probability distribution, i.e. the output of each softmax classifier. Subscript s refers to the point-wise scotoma classifier 34 and subscript d refers to the visual field defect classifier 45. In order to give priority to optimizing the map of quality of vision over the visual field, for $\alpha$ and $\beta$ the following values may for instance be set: $\alpha=0.75$ and $\beta=0.25$. Parameter $\theta$ of the model can be learned through mini-batch gradient descent, for instance using RMSprop for 15,000 iterations with batch size B=128.

Training batches can be formed by first selecting B different sequences from a set of for instance 20-seconds trials, originally sampled at 240 Hz. Then, randomly one sub-sequence of 4.17 seconds (1000 time steps) can be sampled from each sequence and finally be down-sampled to 60 Hz (250 time steps). The luminance level and pursuit type of the corresponding sequences are also added to the training batches.

For determining the visual field defect classification 35 (for the entire visual field), a decision tree (DT) algorithm can be trained to classify and to reduce the dimensionality of the feature-space. Each node of the DT splits the feature space into subspaces, eventually leading to one of a group of possible visual field defects. At each split a decision is based on the decision criterion Gini's Diversity Index (GDI) given as follows:

$1 \Sigma f^2(i)$ where f(i) is the fraction of the number of samples in the training set for class i that reaches a particular node. If a node contains only samples of a unique class then the GDI has a value of 0 and the node is assigned to that class, completing the decision. The classifier's performance is estimated using a 10-fold cross-validation scheme wherein the entire dataset is randomly partitioned into 10 subsets of equal size. Subsequently, nine subsets constitute the training set and the remaining set is used as test set. This process is then repeated until every subset has been used once as a test set. The estimated total accuracy is the average of the accuracies measured after each repetition. This analysis using categorical classifier 45 leads to a categorical classification 35 of the observer visual field defect (e.g.: no defect, central loss, peripheral loss, hemifield loss) that is stored in the storage 5 and can be used by ophthalmologists as a preliminary screening tool to determine what further steps are most likely needed to make a diagnosis.

The models 34 and 45 can be regarded as a mapping y=f(x; $\theta$), where $$y = \begin{bmatrix} p_s \\ p_d \end{bmatrix},$$

$p_s$ being the point-wise scotoma prediction and $p_d$ being the visual field defect prediction 35 of a sub-sequence x.

The data acquisition for one eye can for instance consist of six trials of 20-seconds for each luminance/pursuit combination, the predicted output probability distributions of multiple sub-sequences being averaged. The predictions of 6×2×2=24 down sampled sequences can be averaged. The predicted visual field defect 35 for an eye s of which ocular movement has been measured is thus:

$$y = \arg\max_c \frac{1}{M} \sum_{i: x_i \in S} f(x_i; \theta)$$

where M is the number of sub-sequences in the set of trials S of the eye s of which ocular movement has been measured. In particular, given the time series $p_x(t)$, $s_x(t)$, $p_y(t)$ and $s_y(t)$, together with the luminance and pursuit, the classifier model 34 (FIG. 4) provides a prediction of the scotoma overlap $p_s$ for each down sampled sub-sequence. Then, the sub-sequence predictions of a sequence are concatenated to form the classified time-series 49 of positional deviations, $D_{labeled}$.

In visual field mapping step 50, the set of deviations $D_{labeled}$ is split into two subsets, depending on the labeling. A label value of 1 results in a classification of the specific data point as being obstructed by a scotoma, while a label of 0 results in a classification of the specific data point as not being obstructed by a scotoma.

For determining a quality of view field map 51 of an eye from which measurements have been made, using the trained recursive neural network, each occurrence of the input time-series $D_{labeled}$ is associated with its horizontal and vertical components, respectively $D'_x = p_x(t) - s_x(t)$ and $D'_y = p_y(t) - s_y(t)$, which form the x- and y- components of the position of the stimulus relative to the center of the visual field, which include, for each time point, an estimate of the quality of view at that position relative to the center of the visual field.

In step 50, these components are mapped onto a Cartesian plane of which the origin represents the center of gaze of the eye. In this way, the Cartesian plane forms a representation of the visual field and its center represents the fovea.

In step 50, spatial binning may be applied (e.g. with a bin size equal to one degree of visual field). The value at each bin is then the average of the $D_{labeled}$ values within that bin.

Finally, the calculated map 51 can be stored in the storage 5 and displayed, for instance in a 50×40 grid, covering ±25 degrees of visual field. In this map the severity of visual field loss is indicated (for instance color-coded or in gray scale) and the map can readily be interpreted by ophthalmologists.

Figure 10I:
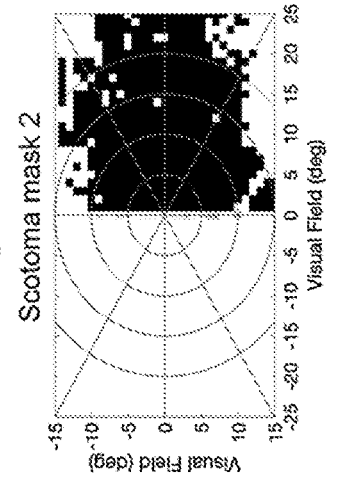
FIG. 10I is map of visual defects obtained from measurement data acquired from a test of performance of the healthy eye with suppression of stimulus display in predetermined positions as shown in FIG. 10G, by RNN processing.

Examples of such visual field maps, resulting from experimental implementation of the described recurrent neural network method, are shown in FIGS. 10C, 10F, and 10I.

FIGS. 10A, 10D and FIG. 10G are maps showing the locations of the scotoma where display of the visual stimulus to be followed was suppressed (black is suppressed, white is not suppressed, grays indicate partial suppression increasing with darkness). More in particular, FIG. 10A shows an example of an unmasked test data map for simulating an eye without visual field loss, FIG. 10D shows an example of a test data mask for simulating an eye suffering from peripheral loss and FIG. 10G shows an example of a test data mask for simulating an eye suffering from hemifield loss.

FIGS. 10B, 10E and 10H show maps reconstructed from measurement results obtained from a healthy eye in which the stimulus to be followed was not masked (FIG. 10B), masked as shown in FIG. 10D (FIG. 10E) and masked as shown in FIG. 10G (FIG. 10H), respectively, using the values provided by the TFCE algorithm described above. The maps reconstructed using the values provided by the TFCE algorithm described above show the accuracy with which the visual field maps of the scotoma that were known a priori is reconstructed on the basis of the measurement of an eye for which the scotoma according to the test data were simulated by (virtual) masking).

FIGS. 10C, 10F and 10I show maps obtained from measurement results obtained from a healthy eye in which the stimulus to be followed was not masked (FIG. 10C), masked as shown in FIG. 10D (FIG. 10F) and masked as shown in FIG. 10G (FIG. 10I), respectively, using the predictions provided by the RNN model described above As can be seen, for both these eyes, the maps reconstructed using the predictions provided by the RNN model described above are almost identical to the maps of the simulated scotoma locations.

Several features have been described as part of the same or separate embodiments. However, it will be appreciated that the scope of the invention also includes embodiments having combinations of all or some of these features other than the specific combinations of features embodied in the examples.

The invention claimed is:

1. A method of measuring a quality of view over a visual field of view of an eye, the method comprising, during a measuring period:
    displaying a stimulus to be followed in a stimulus position in a direction of view relative to an eye,
    moving the stimulus to be followed in a field of view of the eye in varying directions and registering the stimulus positions over time,
    detecting and registering gaze positions in directions of view of the eye following said stimulus to be followed over time,
    determining and registering deviations between the gaze positions and associated ones of the stimulus positions where the stimulus to be followed was displayed when the gaze position was detected and magnitudes of the registered deviations, and
    determining a visual field map of field portions, wherein, for each of said field portions, quality of view is determined in accordance with quality of view estimates of associated ones of the registered deviations of which the associated stimulus positions are located relative to the gaze position so that the associated stimulus positions are in that field portion, and, for each of said associated ones of the registered deviations, the quality of view is estimated in accordance with the magnitude of that associated one of the registered deviations and with magnitudes of at least preceding or succeeding ones of the registered deviations.

2. The method according to claim 1, wherein the stimulus to be followed is moved with varying velocities.

3. The method according to claim 1, wherein gaze positions measured while the gaze position moves with a velocity over a threshold value, stops and moves again with a velocity over the threshold value, are replaced by interpolated gaze positions.

4. The method according to claim 3, wherein positions in a predetermined range of time or sample number prior to and after gaze positions measured while the gaze position moves with a velocity over the threshold value, stops and moves again with a velocity over the threshold value are replaced by interpolated gaze positions.

5. The method according to claim 1, in which the stimulus to be followed is the only moving stimulus being displayed.

6. The method according to claim 1, including the use of a recursive neural network trained using gaze positions obtained by measurements of gaze positions of a healthy eye following a displayed stimulus to be followed.

7. The method according to claim 6, wherein indications for types of visual dysfunctions of the visual field as a whole are determined from registered gaze positions and stimulus positions using the neural network.

8. The method according to claim 7, wherein visual view defects are simulated by suppressing the displaying of the stimulus to be followed in predetermined field portions.

9. The method according to claim 6, wherein data inputted into the recursive neural network during training and during use of the trained recursive neural network include at least one of the following categories of data:
- a maximum value of a correlation between gaze position velocity and stimulus position velocity;
- temporal offset (lag) between gaze position and stimulus position;
- temporal precision of gaze position relative to stimulus position;
- variance explained by a Gaussian model fitted to a correlogram of gaze positions velocities and stimulus position velocities against time delay;
- number of occurrences of a most likely deviation of the gaze position from the stimulus position;
- average spatial offset (bias) between the gaze position and the stimulus position;
- average deviation of the gaze position from the stimulus position; and
- variance of the deviation of the gaze position from the stimulus position explained by a Gaussian model fitted to a graph of occurrences of deviations in a plurality of ranges.

10. The method according to claim 1, wherein the stimulus position is moved continuously during the measurement period.

11. The method according to claim 1, wherein the determination of the quality of view for each associated one of the registered deviations is carried out by integration over a series of the registered deviations, said series:
- starting from a starting one of said series of the registered deviations having a magnitude at or below a minimum threshold magnitude $h_0$;
- including a first succession of the registered deviations having magnitudes increasing up to a magnitude h of said associated one of the registered deviations;
- including said associated one of the registered deviations; and
- including a second succession of the registered deviations having magnitudes decreasing from said magnitude h of said associated one of the registered deviations to a closing one of said series of the registered deviations, having a magnitude at or below the minimum threshold magnitude $h_0$; and
- forming an uninterrupted succession of the registered deviations of which, except for said starting one of said series of the registered deviations and said closing one of said series of the registered deviations, the magnitudes are larger than the minimum threshold magnitude $h_0$.

12. The method according to claim 11, wherein, prior to the integration over the series of the registered deviations, the magnitudes of the series of the registered deviations that are larger than h are reduced to a capping value in accordance with the magnitude h.

13. The method according to claim 1, wherein the determination of the quality of view for each field portion is carried out using a recursive neural network trained to obtain a recurrent neural model with:
- training input comprising a series of training time points each including a stimulus position, being the position of the stimulus to be followed, and a gaze position of a healthy eye following the stimulus to be followed, and an indication for each training time point, whether the stimulus position relative to the gaze position is in a field portion where displaying of the stimulus to be followed was suppressed, and
- training output comprising a map of field portions where displaying of the stimulus to be followed was suppressed during a measurement session for obtaining the training input.

14. The method according to claim 13 wherein, in operation, the method comprises:
- inputting a series of time points each including a stimulus position, being the position of the stimulus to be followed, and a gaze position of an eye to be examined following the stimulus to be followed;
- the trained recursive neural network classifying the visual qualities of the series of time points into scotoma time points at locations in the field of vision where vision is classified to be functional and non-scotoma time points at locations in the field of vision where vision is classified to be dysfunctional;
- determining for each of the field portions which time points have a deviation such that the stimulus position relative to the gaze position is in that field portion; and
- generating a visual field map indicating, for each of the field portions, an aggregated vision quality value in accordance with the estimated visual qualities of the time points having a stimulus position determined to be in that field portion.

15. The method according to claim 13, wherein the recursive neural network includes fully connected layers in which all output units are connected to all input units and vice versa and at least one gated recurrent unit that processes sequential information in a recurrent way with long short-term memory capabilities to capture time dependencies.

16. The method according to claim 15, further comprising:
- capturing and inputting luminance and pursuit data during the measurement period;
- at least two fully connected layers processing the luminance and pursuit data into categorical data indicating types of scotoma;
- inputting a combination of the time points from the gated recurrent unit and the categorical data into a softmax classifier of the recurrent neural network; and
- the softmax classifier predicting for each time point whether, the stimulus position of that time point is in a location in the visual field, which is over a scotoma.

17. A system for measuring quality of view over a visual field of view of an eye, the system comprising:
- a display;
- an eye-tracker for tracking gaze positions in a direction of view of an eye on the display;
- a data processor system including a video display controller, connected to the display for controlling the display for displaying a visual stimulus to be followed in a stimulus position moving over the display and connected to the eye tracker for receiving data representing the gaze positions from the eye tracker, the data processor system being programmed for, during a measuring period:
- causing the display to display the stimulus to be followed to be displayed in the stimulus positions,
- receiving data representing the gaze positions from the eye-tracker,
- causing the display to move the stimulus to be followed over the display in varying directions and registering the stimulus positions over time,
- registering the received gaze positions over time,
- determining and registering deviations between the gaze positions and associated ones of the stimulus positions where the stimulus to be followed was displayed when the gaze position was detected and magnitudes of the deviations, and determining a visual field map of field portions, wherein, for each of said field portions, quality of view is determined in accordance with the quality of view estimates of associated ones of the registered deviations of which the associated stimulus positions are located relative to the gaze position so that the associated stimulus positions are in that field portion, and, for each of said associated ones of the registered deviations, the quality of view is estimated in accordance with the magnitude of that associated one of the registered deviations and with magnitudes of at least preceding or succeeding ones of the registered deviations.

18. A computer program product stored in a computer readable form, the computer program, when executed on a computer causes the computer to:

control a display for displaying a stimulus to be followed in stimulus positions, receive data representing gaze positions on the display, control the display for moving the stimulus to be followed over the display in varying directions and registering the stimulus positions over time, register the received gaze positions over time, determine and register deviations between the gaze positions and associated ones of the stimulus positions where the stimulus to be followed was displayed when the gaze position was detected and magnitudes of the deviations, and determine a visual field map of field portions, wherein, for each of said field portions, quality of view is determined in accordance with the quality of view of associated ones of the registered deviations of which the associated stimulus positions are located relative to the gaze position so that the associated stimulus positions are in that field portion, and, for each of said associated ones of the registered deviations, the quality of view is estimated in accordance with the magnitude of that associated one of the registered deviations and with magnitudes of at least preceding or succeeding ones of the registered deviations.

* * * * *